United States Patent
Ghosh et al.

(10) Patent No.: US 11,615,881 B2
(45) Date of Patent: Mar. 28, 2023

(54) LIVER CANCER DETECTION

(71) Applicant: HEPATIQ, INC., Irvine, CA (US)

(72) Inventors: Dipankar Ghosh, Irvine, CA (US); John Carl Hoefs, Irvine, CA (US)

(73) Assignee: Hepatiq, Inc., Irvine, CA (US)

( * ) Notice: Subject to any disclaimer, the term of this patent is extended or adjusted under 35 U.S.C. 154(b) by 247 days.

(21) Appl. No.: 17/095,482

(22) Filed: Nov. 11, 2020

(65) Prior Publication Data

US 2021/0142891 A1    May 13, 2021

Related U.S. Application Data (60) Provisional application No. 62/934,449, filed on Nov. 12, 2019.

(51) Int. Cl.
| | |
|---|---|
| *G06T 7/62* | (2017.01) |
| *G16H 30/40* | (2018.01) |
| *G06T 7/00* | (2017.01) |
| *G06T 7/20* | (2017.01) |
| *G06T 5/00* | (2006.01) |

(52) U.S. Cl.
CPC .............. *G16H 30/40* (2018.01); *G06T 5/001* (2013.01); *G06T 7/0012* (2013.01); *G06T 7/20* (2013.01); *G06T 7/62* (2017.01); *G06T 2207/10108* (2013.01); *G06T 2207/20224* (2013.01); *G06T 2207/30056* (2013.01); *G06T 2207/30096* (2013.01)

(58) Field of Classification Search
CPC ......... G16H 30/40; G06T 7/62; G06T 7/0012; G06T 7/20; G06T 5/001; G06T 2207/10108; G06T 2207/20224; G06T 2207/30056; G06T 2207/30096
See application file for complete search history.

(56) References Cited

U.S. PATENT DOCUMENTS

| | | | |
|---|---|---|---|
| 8,768,022 B2 * | 7/2014 | Miga ...................... | G06T 7/344 382/128 |
| 11,049,245 B2 * | 6/2021 | Hattori ................... | G06T 7/0012 |
| 2010/0128946 A1 * | 5/2010 | Fidrich ..................... | G06T 7/11 382/131 |
| 2010/0135453 A1 * | 6/2010 | Mendonca ........... | A61B 6/4241 378/5 |

(Continued)

OTHER PUBLICATIONS

Moghbel, M., Mashohor, S., Mahmud, R. et al. Review of liver segmentation and computer assisted detection/diagnosis methods in computed tomography. Artif Intell Rev 50, 497-537 (2018). https://doi.org/10.1007/s10462-017-9550-x.*

(Continued)

*Primary Examiner* — Shefali D Goradia
(74) *Attorney, Agent, or Firm* — Knobbe, Martens, Olson & Bear, LLP (57) ABSTRACT

Methods and systems for determining a tumor volume from image data obtained from a functional scanner. The methods and systems can include identifying a portion within a region of interest corresponding to a liver that varies in intensity with its corresponding neighboring portion by a threshold. The method and systems can further include determining a volume of the portion without identifying a boundary of the portion. The portion can also be tracked over time. The image data can include a scan from a SPECT scanner.

18 Claims, 11 Drawing Sheets

(56) References Cited

U.S. PATENT DOCUMENTS

| | | | | |
|---|---|---|---|---|
| 2012/0150048 A1* | 6/2012 | Kang | .................... | G06T 7/149 |
| | | | | 600/481 |
| 2015/0078640 A1* | 3/2015 | Guo | ...................... | G06T 7/12 |
| | | | | 382/131 |
| 2015/0356730 A1* | 12/2015 | Grove | .................... | G06T 7/64 |
| | | | | 382/124 |
| 2016/0217262 A1* | 7/2016 | Sharbell | ................. | G06N 20/10 |
| 2018/0276821 A1* | 9/2018 | Lin | ...................... | G16H 50/30 |

OTHER PUBLICATIONS

Kitamura, Kei, et al. "Registration accuracy and possible migration of internal fiducial gold marker implanted in prostate and liver treated with real-time tumor-tracking radiation therapy (RTRT)." Radiotherapy and oncology 62.3 (2002): 275-281.*

* cited by examiner

LIVER CANCER DETECTION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

The human body cannot live without an adequately functioning liver. Liver function (LF) affects digestion, metabolism and detoxification. Liver cancer (LC) is a life-threatening disease. Cancerous liver cells do not function normally and may divide uncontrollably. As a result, they may crowd out healthy liver cells and invade other parts of the body. LC is often seen in cirrhotic patients with reduced LF.

Common symptoms of advanced LC include poor appetite, weight loss, nausea, fatigue, abdominal pain, abdominal swelling and jaundice. However, these symptoms are not specific to LC as other conditions can cause similar symptoms and are not present early when the tumor is small. A diagnosis of LC involves blood tests, imaging tests, and/or a liver biopsy. LC caught in earlier stages will have better therapy outcomes than those caught in advanced stages. Patients at high risk for LC include those with chronic liver disease from infections (hepatitis B or C), fatty liver, and genetic conditions (hemochromatosis, etc.). These patients may also have reduced or deteriorating LF. They may receive more vigorous monitoring using blood and imaging tests.

SUMMARY OF THE INVENTION

The systems and methods described herein can be implemented by a computer system comprising computer hardware. The computer system may include one or more physical computing devices, which may be geographically dispersed or co-located.

Certain aspects, advantages and novel features of the inventions are described herein. It is to be understood that not necessarily all such advantages may be achieved in accordance with any particular embodiment of the inventions disclosed herein. Thus, the inventions disclosed herein may be embodied or carried out in a manner that achieves or selects one advantage or group of advantages as taught herein without necessarily achieving other advantages as may be taught or suggested herein.

In certain aspects, a system for determining a tumor from image data obtained from a functional scanner can include one or more hardware processors. The one or more hardware processors can determine a region of interest corresponding to an anatomical feature from image data taken at a first time. The one or more hardware processors can also identify a portion within the region of interest that varies in intensity with its corresponding neighboring portion by a threshold. The one or more hardware processors can also fit a shape from the identified portion that corresponds to a suspected tumor mass. The one or more hardware processors can track the fitted shape over time with image data obtained at a second time of the same anatomical feature. The one or more hardware processors can determine that the fitted shape corresponds to a tumor based on the tracking.

The system of the preceding paragraph can further include one or more of the following features: determine a volume of the tumor without identifying a boundary of the tumor, wherein the volume of the tumor is further determined based on a concentration of isotope intensities corresponding to functioning tissue, wherein the volume of the tumor is further determined based on subtracting a functioning tissue volume in a shape including the tumor from the shape's volume, wherein the fitted shape comprises a 3D ellipsoid, wherein the fitted shape comprises a 3D tubular shape, determine that the fitted shape corresponds to a blood vessel or a cyst, pre-process the image data, wherein the pre-processing comprises at least one or more of: boosting resolution, sharpening, slicing, or dicing, display results of the determination, wherein the image data is a SPECT scan, and wherein the region of interest correspond to a liver.

In certain aspects, a method for determining a tumor from image data obtained from a functional scanner can include determining a region of interest corresponding to an anatomical feature from image data taken at a first time. The method can further include identifying a portion within the region of interest that varies in intensity with its corresponding neighboring portion by a threshold. The method can also include fitting a shape from the identified portion that corresponds to a suspected tumor mass. The method can further include tracking the fitted shape over time with image data obtained at a second time of the same anatomical feature. The method can also include determining that the fitted shape corresponds to a tumor based on the tracking.

The method of the preceding paragraph can further include one or more of the following features: determine a volume of the tumor without identifying a boundary of the tumor, wherein the volume of the tumor is further determined based on a concentration of isotope intensities corresponding to functioning tissue, wherein the volume of the tumor is further determined based on subtracting a functioning tissue volume in a shape including the tumor from the shape's volume, wherein the fitted shape comprises a 3D ellipsoid, wherein the fitted shape comprises a 3D tubular shape, determine that the fitted shape corresponds to a blood vessel or a cyst, pre-process the image data, wherein the pre-processing comprises at least one or more of: boosting resolution, sharpening, slicing, or dicing, display results of the determination, wherein the image data is a SPECT scan, and wherein the region of interest correspond to a liver.

In certain aspects, a system for determining a tumor volume from image data obtained from a functional scanner can include one or more hardware processors. The one or more hardware processors can identify a portion within a region of interest corresponding to a liver that varies in intensity with its corresponding neighboring portion by a threshold. The one or more hardware processors can determine a volume of the portion without identifying a boundary of the portion. In some instances, the volume is confirmed as a tumor based on fitting a shape from the identified portion. In additional instances, the volume is further confirmed as the tumor based on tracking the portion over time.

BRIEF DESCRIPTION OF THE DRAWINGS

Embodiments disclosed herein are described below with reference to the drawings. Throughout the drawings, reference numbers are re-used to indicate correspondence between referenced elements. The drawings are provided to illustrate embodiments of the inventions described herein and not to limit the scope thereof.

DETAILED DESCRIPTION OF THE PREFERRED EMBODIMENT

Simultaneously Measuring LF and Detecting LC

Blood tests do not provide quantitative LF and generally will not detect LC with specificity. Most blood tests (albumin, INR, liver enzymes, AFP, etc.) do not become abnormal in the early stages of LC. Moreover, blood tests can be significantly abnormal in patients without LC. For example, nephrotic syndrome or coeliac disease can cause loss of albumin so that the levels in blood are low. Many patients with early LC have normal AFP levels. Also, AFP levels can be increased from other kinds of cancer as well as some non-cancerous conditions. Thus, monitoring patients with blood tests may not detect early stages of LC and will not provide quantitative LF.

Imaging tests are generally more expensive than blood tests and include elastography and anatomic imaging. Elastography does not quantify LF but measures liver stiffness. This provides an indication of the amount of scarring in the liver but may not detect LC. Anatomic imaging includes ultrasound, CT and MRI. They do not provide quantitative LF but may show a tumor if it is large enough. They may miss early LC tumors. Current functional imaging techniques can measure LF but may not detect LC.

Thus, current tests are unable to simultaneously measure LF and detect LC. Disclosed herein are systems and methods of simultaneously measuring LF and detecting LC. The systems and methods also applies to detecting cancer in other organs besides the liver. The systems and methods also apply to other pathologies besides cancer and to detecting cancer with or without use of molecular cancer tagging agents.

Differentiating Masses in Low Resolution Images

Functional imaging, such as SPECT, is currently used to measure LF. A detailed disclosure for determining LF from SPECT scan is described in U.S. Pat. No. 10,076,299 assigned to Hepatiq Inc., incorporated by reference herein in its entirety (hereinafter, the '299 patent). SPECT images are typically low resolution images and it is difficult to visualize a tumor in such images especially when they are small. Furthermore, any attempt to visualize such tumors requires a trained medical specialist to painstakingly search through numerous image frames or comb through 3D reconstructions to attempt to spot a tumor. This is an error prone process and subjective because it depends on the training of the medical specialist and their judgement. Accordingly, many early stage tumors are missed. Furthermore, other masses, such as vessels, may be mistaken for tumor masses.

Thus, current functional imaging techniques are not suitable for locating tumor masses and distinguishing them from other masses such as vessels through visual inspection. Accordingly, the systems and methods described herein automatically locate masses and distinguish between tumor masses and other structures.

Measuring Changes in Tumor Volume

One important characteristic of tumors is that they grow rapidly compared to other liver masses, such as cysts. Accordingly, it was realized that the rate of change of tumor volume can be used to distinguish between tumors and other liver masses in SPECT images. However, measuring tumor volume by determining the boundary of the tumor is not very accurate as the boundaries depend on chosen threshold levels and these can be affected by many factors from one scan to the next. Furthermore, detecting small changes in volume in low resolution SPECT images may be virtually impossible if boundaries are being used.

Thus, current image processing techniques are not very accurate in detecting small changes in tumor volume from one scan to the next. Accordingly, in some instances, the systems and methods of calculating tumor volume described below do not depend on determining the tumor boundary. Therefore, in some instances, it may not be necessary to perform a boundary analysis.

The systems and methods described herein automatically analyze liver images to simultaneously quantify LF and detect LC. In some instances, the systems and methods automatically distinguish liver tumors from other masses. In some instances, the systems and methods automatically measure tumor volume without relying on exact determination of tumor boundaries. For the sake of brevity, the system will be referred to as (LCAW) below.

LCAW System

Figure 1:
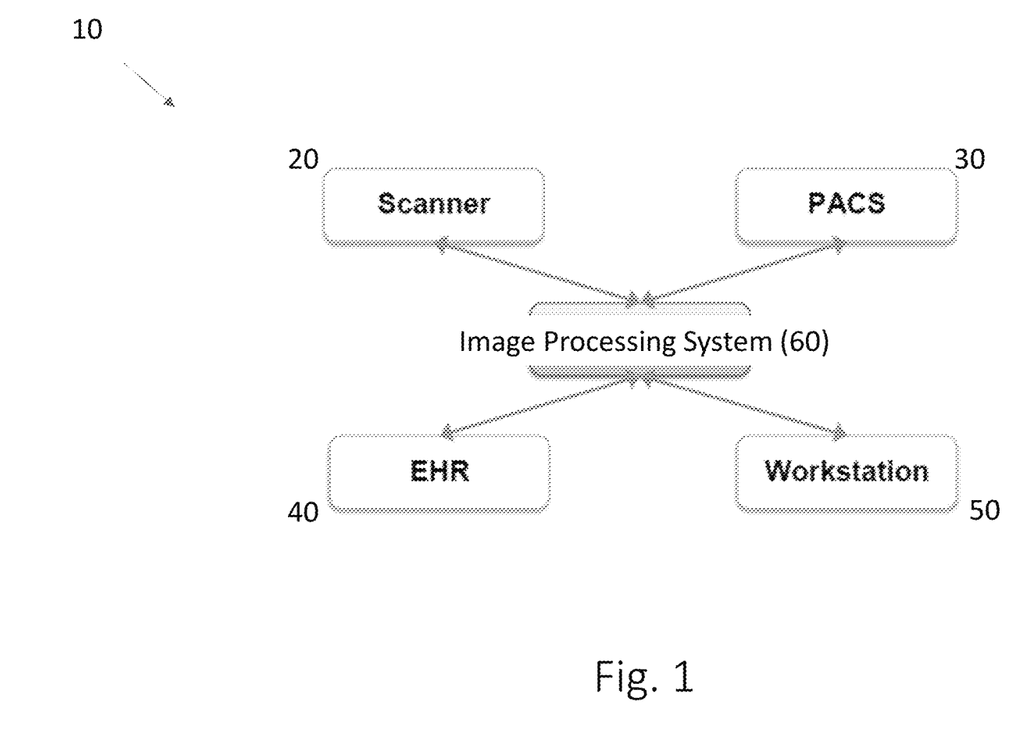
FIG. 1 illustrates an embodiment of a computing environment including an image processing system can enable clinicians to identify a tumor, determine a tumor volume, or track tumors.

FIG. 1 is a block diagram of an exemplary LCAW system 10.

Scanner

The LCAW system 10 includes a Scanner 20 such as a Single Photon Emission Computed Tomography (SPECT) scanner. Exemplary SPECT and hybrid SPECT/CT scanners are commercially available from several manufacturers such as General Electric Healthcare. The SPECT scanner is used to take liver images of the patient. Other scanner technologies, such as PET, PET/CT, CT, MRI, fMRI, ultrasound, x-ray, fluoroscope may also be used in the LCAW system.

PACS

The LCAW system may include a Picture Archiving and Communications System (PACS) 30. Liver images of the patient taken on the Scanner 20 are typically transferred to the PACS 30 for storage. Exemplary PACS are commercially available from vendors such as McKesson Radiology. Other image storage systems including the Scanner itself can also be used in the LCAW system.

EHR

The LCAW system includes an Electronic Health Records (EHR) system 40. Patient data, including demographics, clinical indications, medications, history, etc. can be retrieved from the EHR 40 by the image processing system (IPS) 60 as described below. Exemplary EHR are commercially available from vendors such as EPIC. Other health data storage systems may also be used.

Workstation

In some instances, the LCAW 10 can include a Workstation 50 for executing the IPS 60. The Workstation 50 can be any computing device including one or more hardware processors, such as a personal computer, a server, mobile computing devices, scanners, ASICs, or FPGAs. In some instances, the workstation 50 may only execute a portion of the IPS 60, such as display of the parameters or results of the analysis described herein.

Image Processing System

An image processing software system 60 includes software instructions that can be executed one or more hardware systems such as the workstation 50. The IPS 60 can analyze the liver images and measure LF and detect LC. The results can be included in a report, which can be displayed on one or more user interfaces.

In some instances, the IPS 60 is divided into five engines or sub-programs: (a) PACS Interface, (b) EHR Interface, (c) LCAW Analyzer, (d) LCAW Detector, and (e) LCAW Reporter. In some instances, the PACS 30 Interface transfers liver images from PACS 30 to the Workstation 50 and transfers LCAW Reports from the Workstation 50 to PACS 30. The EHR Interface can transfer patient data from the EHR 40 to the Workstation 50 and LCAW Reports from the Workstation 50 to HER 40. The LCAW Analyzer can process liver images and measure LF and associated parameters. The LCAW Detector can process liver images and detect LC and associated parameters. The LCAW Reporter can generate the LCAW Report for display. While the IPS 60 is shown as divided into these sub-modules, additional modules can also be part of the software. Furthermore, the modules can be distributed over multiple hardware processors over a network.

LCAW Method

Figure 2:
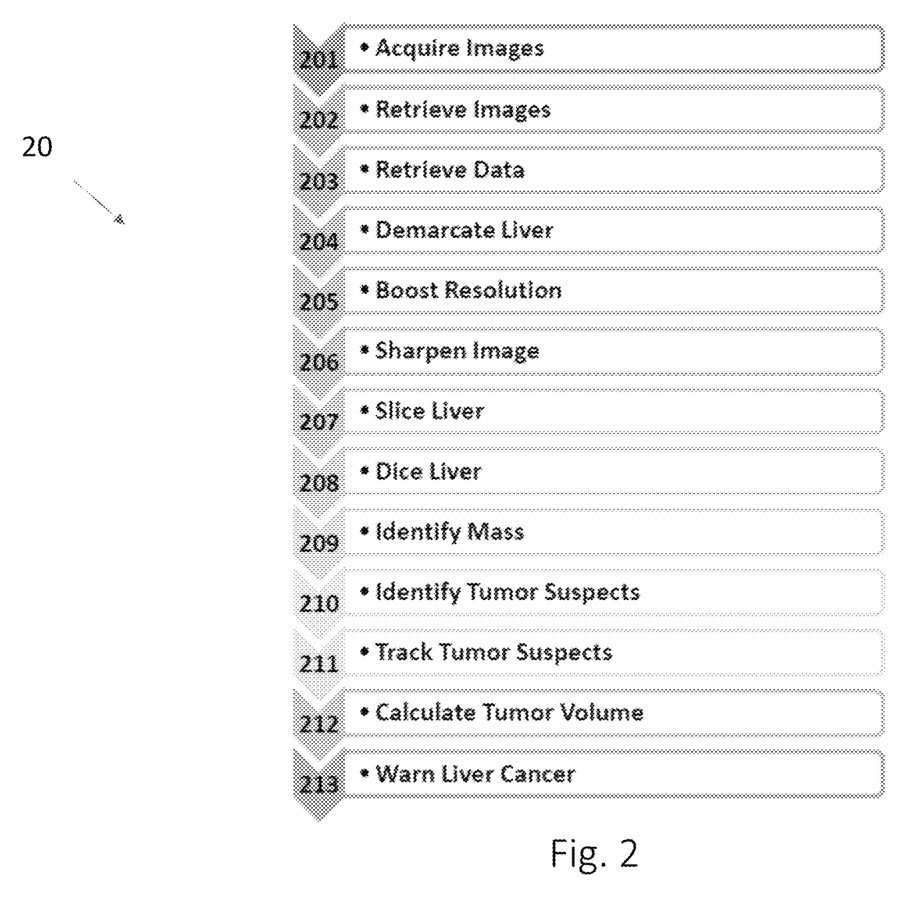
FIG. 2 illustrates a flowchart of an embodiment of a process for determining liver cancer.

FIG. 2 is a flowchart representing an embodiment of a process 20 for detecting liver cancer. For the sake of clarity, the steps are shown in a linear order. However, in some instances, only some of the steps shown in the flowchart may be performed by the IPS 60. Furthermore, in some instances, the steps shown in the flowchart can be performed out of order. In additional instances, some of the steps may be performed in parallel. In some instances, some of the steps can be performed on a scan at a first time and the remaining steps may be performed at a later time on the same scan or a new scan acquired at the later time. For example, in some instances, tracking of tumor may be an independent process compared to calculating a volume of tumor. Furthermore, some of the steps may be omitted. For example, some of the pre-processing steps may be omitted.

Acquire Images 201

In an embodiment, the patient is injected with a sulfur colloid (SC) solution labeled with a radionuclide such as Technetium-99 metastable (T99m) and transverse images acquired of the liver using the Scanner 20. Other suitable solutions and radionuclides can also be used. The IPS 60 could employ other image views, such as, anterior, posterior, oblique, sagittal, coronal, reformatted, secondary captures, or derived images. The IPS 60 can also operate on raw scanner data rather than image data.

The acquired images are typically stored on the scanner temporarily and transferred to PACS 30 for long-term storage. It is understood that the archived images may or may not be encrypted. In some embodiments, the IPS 60 analyzes images in Digital Imaging and Communication in Medicine (DICOM) format.

Retrieve Images 202

The IPS 60 can automatically retrieve the transverse SPECT liver images from the PACS 30. The images may be retrieved using the DICOM protocols, although other protocols could be used. Images can also be retrieved directly from the Scanner 20 or from some other archival device such as CD, DVD, workstation, network or the internet. Also, it is understood that images may be automatically or manually transmitted from the source (Scanner or archival device) to the Workstation 50 or other computing system executing IPS 60.

Retrieve Data 203

The IPS 60 can automatically retrieve patient data, including demographics, clinical indications, medications, history, physician orders, etc. from the EHR 40 to the Workstation 50. Data can be retrieved using the HL/7 protocols, although other protocols could be used. Data may also be retrieved directly from the patient or from some other information source. Also, it is understood that data may be automatically or manually transmitted from the source rather than being retrieved.

Demarcate Liver 204

Figure 3:
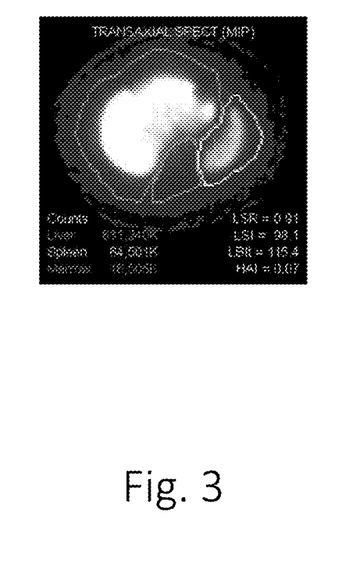
FIG. 3 illustrates identified region of interest in a SPECT scan.

The images are processed by IPS 60 to automatically identify the liver, spleen and marrow boundaries as described in more detail in the '299 patent. Liver function and associated parameters are calculated as described in the '299 patent. FIG. 3 illustrates identified liver, spleen, and marrow boundaries along with the associated liver function parameters.

Boost Resolution 205

Figure 4:
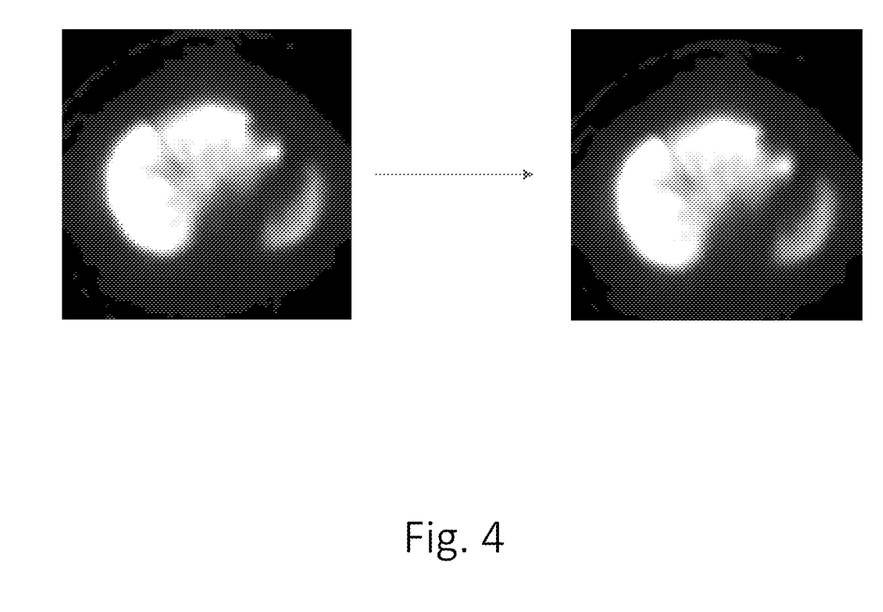
FIG. 4 illustrates an application of resolution boosting processing of received image.

In some instances, the images can be processed by the IPS 60 to enhance their resolution as illustrated in FIG. 4. In some embodiments, the resolution is boosted by a factor of 4 in each of the three dimensions as illustrated in FIG. 4. It is understood that higher boost factors may be used.

In some embodiments, resolution enhancement is performed using voxel interpolation in 3 dimensions. It is understood by those skilled in the art, that other techniques for resolution enhancement may be employed, including wavelet transforms, deconvolution, etc.

Sharpen Image 206

Figure 5:
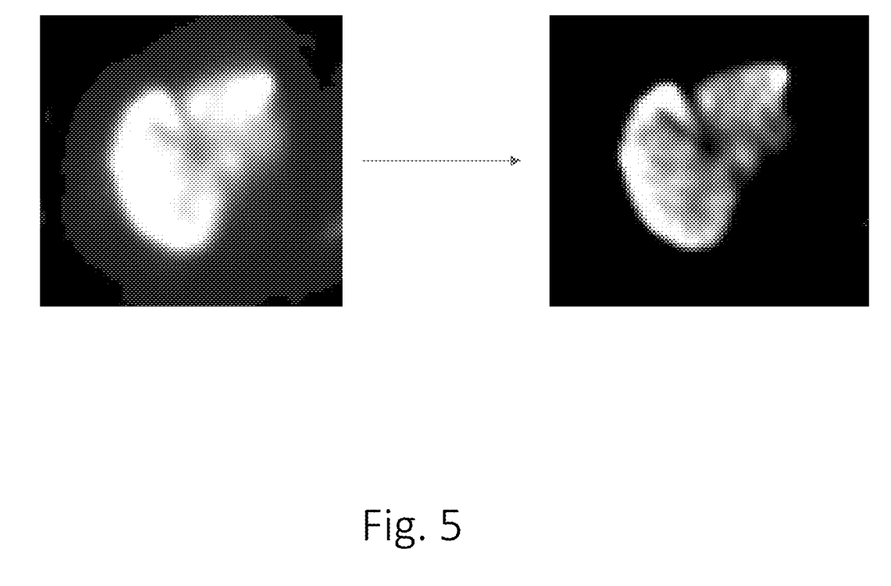
FIG. 5 illustrates an application of sharpening processing on the enhanced image of FIG. 4.

The boosted image can be sharpened with a sharpening filter as illustrated in FIG. 5. In some embodiments, a 7×7 filter is used. It is understood that other filter sizes may be used. Sharpening is accomplished by convolving a frame of pixels with a sharpening filter. It is understood that the method can be applied in all three dimensions.

It is understood by those skilled in the art that the filter may be used to deconvolve the inherent physical characteristics of a functional imaging device such as SPECT, PET or fMRI. Alternatively, blind deconvolution techniques may be used.

Slice Liver 207

Figure 6:
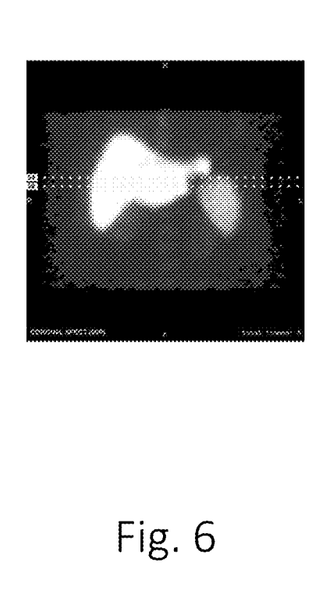
FIG. 6 illustrates a visualization of segmentation of a SPECT image into a slice.

The liver can be segmented into a plurality of slices by IPS 60 as shown in FIG. 6. The raw voxel data from the Scanner may be organized into slices. However, these slices typically are quite thick and may overlap each other. Thus, by themselves they may not be suitable for locating suspected tumor masses. Accordingly, IPS 60 can transform the raw Scanner slices to secondary slices that offset the slice overlap. In some instances, weighted averages are used. It is understood by those skilled in the art that other techniques such as interpolation and deconvolution could be used. The thickness of the secondary slices are adjusted to aid in the detection of tumor masses. In some embodiments, the slice thickness is selected to be 2 voxels initially. Slice thickness can also be 4, 6, 8, or more voxels.

It is understood that the secondary slice thickness may be iteratively made smaller or larger to identify smaller or larger masses. It is also understood that iterative search time may be reduced by techniques known to those skilled in the art such as depth-first or breadth-first search. It is also understood that curved slices and variable thickness slices may be used to optimize search results.

Dice Liver 208

Figure 7:
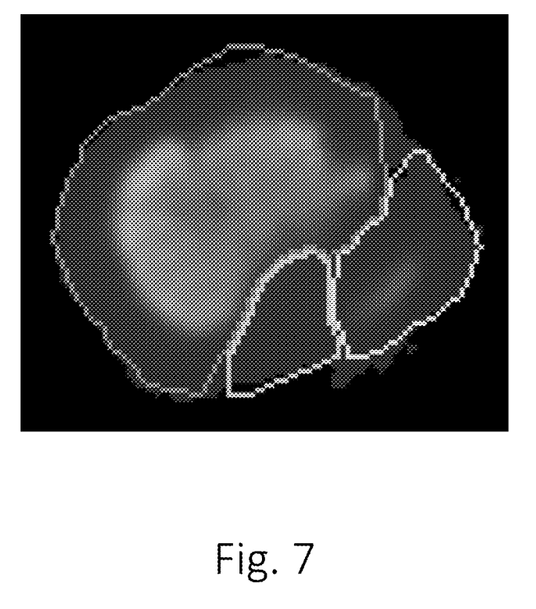
FIG. 7 illustrates a visualization of a cube as a result of dicing into a plurality of volume elements.

Once a secondary slice is selected, it can be diced into a plurality of volume elements, such as a cube as shown in FIG. 7. In some embodiments, the cube dimensions are 5×5×5 voxels for a volume of 125 voxels.

It is understood that the cube size may be iteratively made smaller or larger to identify smaller or larger masses. It is also understood that iterative search time may be reduced by techniques known to those skilled in the art such as depth-first or breadth-first search. It is also understood that curved cubes and variable cube sizes may be used to optimize search results. Furthermore, non-cubic geometries may be used for improved performance.

Identify Mass 209

Figure 8:
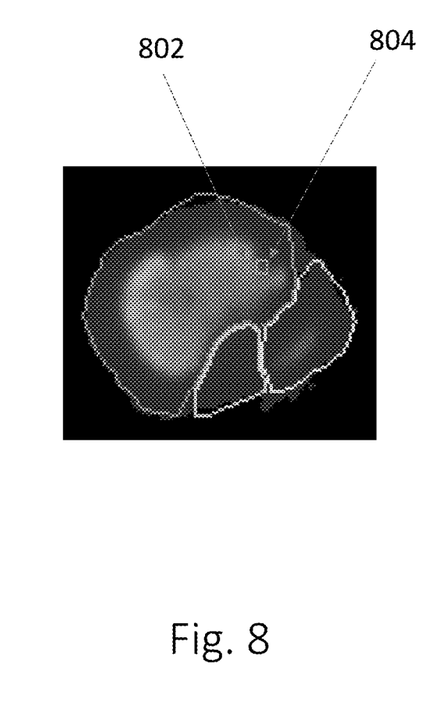
FIG. 8 illustrates a visualization of neighboring cubes for determination of a mass that has an average intensity deviating from a neighbor.

Once the liver is diced, radioisotope intensities in neighboring cubes, such as 802 and 804, may be compared by IPS 60 to detect masses such as tumors, cysts, and vessels as shown in FIG. 8. In some instances, the IPS 60 can iteratively compare neighboring cubes across the entire organ, such as the liver.

Figure 9:
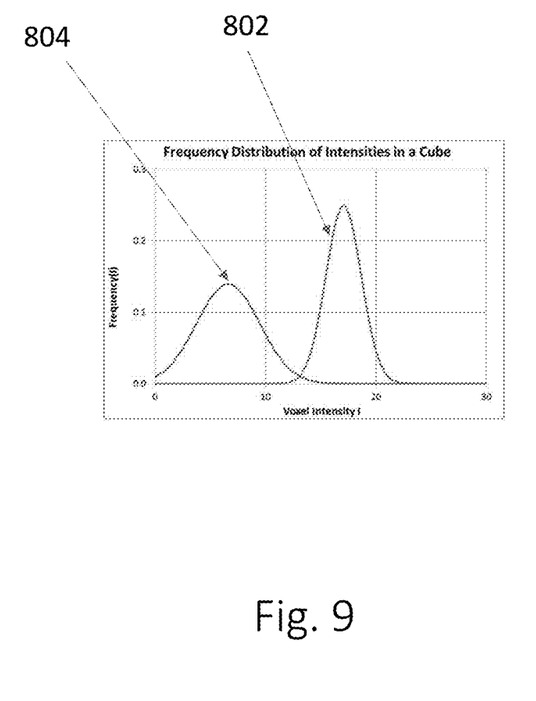
FIG. 9 illustrates a histogram of intensities of neighboring cubes.

In some embodiments, the comparison between neighboring cube is performed by computing a histogram distribution of the radioisotope counts and applying a threshold to the differences. The cube 802 in FIG. 8 has higher intensities than the neighboring cube 804, as shown in FIG. 9.

It is understood that the method may be applied to imaging modalities where the suspect cube intensities are more (hotter) or less (colder) than neighboring cube intensities. It is understood that touching and non-touching neighbors may be used, and the size of the comparison neighborhood may be increased or decreased for optimal performance. It is understood by those skilled in the art, that other techniques may be used to identify masses, such as, pattern recognition, transform methods, fuzzy logic, neural networks, etc.

Identify Tumor Suspects 210

Figure 10A:
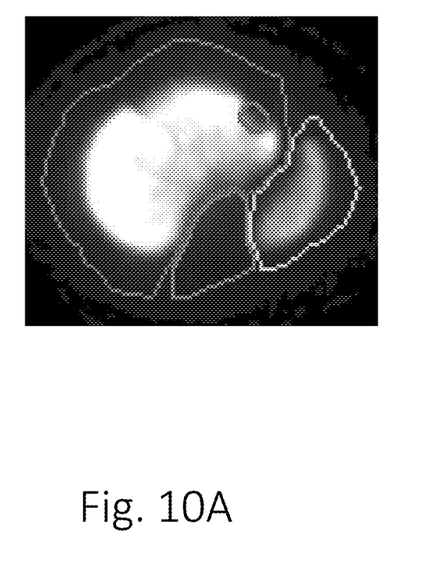
FIG. 10A illustrates an example of fitting a shape on an identified mass.

Once a mass is identified as a tumor suspect, its 3-dimensional shape can be determined. In some embodiments, a 3D ellipsoid is fitted by IPS 60 to the identified mass. The 3D parameters of the ellipsoid, such as, axes lengths, eccentricities, volume, etc. can be determined by IPS 60. In additional embodiments, a 3D tubular shape can be fitted to the identified Mass. The 3D parameters of the tube, such as, length, radius, spiral, volume, etc. can be determined by IPS 60. The distribution of the voxel intensities inside the ellipsoid or tube shapes are determined. The tube and ellipsoid parameters together with the intensity distributions can be used to identify cysts and blood vessels. For example, cysts and blood vessels may form a regular shape as compared to a tumor. Accordingly, the IPS 60 may compare the shape and/or shape parameters with stored values to label the mass. In some instances, machine learning techniques may be used for the purposes of initial labeling. The IPS 60 can label the remaining masses as suspected tumor masses. These labels can be stored in a memory.

It is understood that other 3D shapes may be employed besides ellipsoids and tubes. These include spheres, cubes, torus, cylinder, cone, cuboid, pyramid, prism, etc. It is also understood that nearby masses may be connected before parameters and distribution are determined. It is also understood that touching masses may be separated before parameters and distribution are determined. It is understood that other masses, such as, cysts and vessels may appear like tumor masses. By fitting multiple 3D shapes to the same suspected mass and tracking changes to fitting parameters over time, the present invention is able to distinguish between true tumors and other masses.

Track Tumor Suspects 211

If a scan is repeated over time, the suspected tumor is not likely to appear in the same place in the repeat image. This is because of many factors, such as, changes in the body due to weight gain or loss, changes in the liver due to cirrhosis progression, changes in liver volume due to fat build-up, growth of the tumor, etc. Furthermore, position of the patient in the scanner from one scan to the next, scan parameters and dose used, reconstruction parameters used, etc. can make the suspected tumor shift in the image. This is illustrated in the FIGS. 10A and 10B, which shows a liver tumor in the same patient on scans taken a few months apart.

Figure 10B:
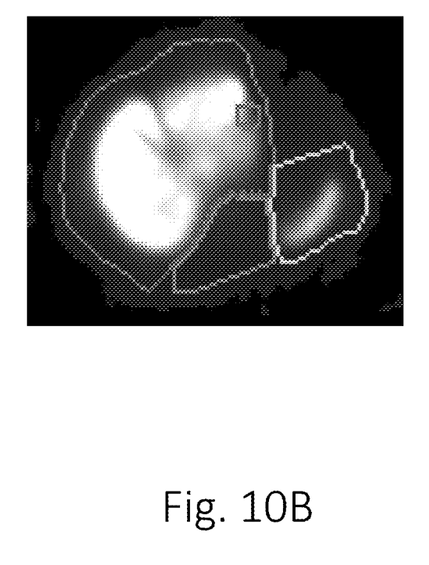
FIG. 10B illustrates tracking the fitted shape over time in a subsequency scan.

The parameters of the 3D shape fitted to the tumor from scans across time periods can be compared and a multi-parameter threshold can be used to confirm it is the same tumor suspect. As discussed above, cysts and blood vessels may not grow or move over time. Accordingly, the IPS 60 can also use temporal variations to confirm or reject tumor suspects from prior scans. Otherwise a new tumor suspect is identified. In some instances, the IPS 60 can use tracking filters such as Kalman filter or Markov models to track the tumor.

Calculate Tumor Volume 212

Figure 11:
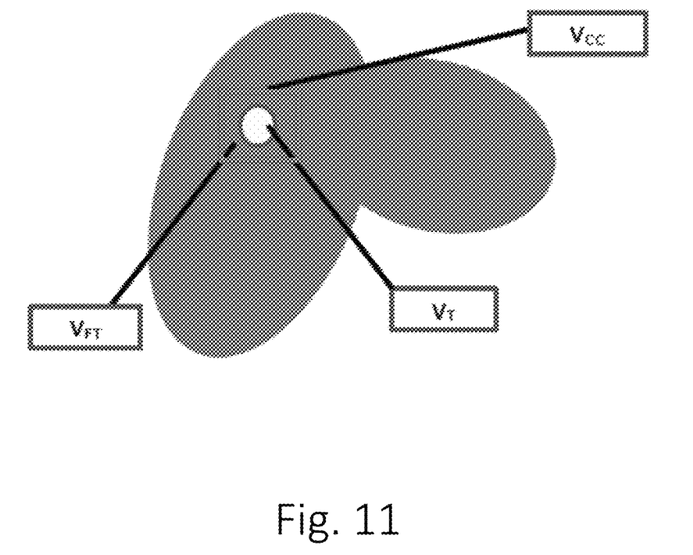
FIG. 11 illustrates a visualization of a determination of tumor volume without identifying a boundary of the tumor.

Tumor volume is an important parameter in clinical decision making regarding the type and timing of therapeutic interventions. Several imaging techniques try to measure the tumor volume based on measuring a boundary of the tumor. However, this is not always accurate because the boundaries may depend on the chosen threshold levels which can vary between scans. Furthermore, SPECT scans have low resolution compared to MRI and it may be difficult to identify a tumor volume for a small tumor. Furthermore, the following factors may also affect the boundary determination: changes in the body due to weight gain or loss, changes in the liver due to cirrhosis progression, changes in liver volume due to fat build-up, etc. Furthermore, position of the patient in the scanner from one scan to the next, scan parameters and dose used, reconstruction parameters used, etc. can make the suspected tumor boundaries appear different.

Accordingly, the IPS 60 can calculate tumor volume without identifying a boundary of the tumor or a contour of tumor mass. Therefore, in some instances, the IPS 60 may precisely track tumor volume changes on serial scans without using boundary or contour analysis to identify tumor boundaries.

The IPS 60 can calculate volume of the tumor ($V_T$) as a difference between the volume of a circumscribing cube ($V_{CC}$) and the volume of functioning tissue ($V_{FT}$) in the circumscribing cube, ie, $V_T = V_{CC} - V_{FT}$. The size of the cube can be selected to encompass suspected tumor. It is understood that the circumscribing cube may be much larger than the tumor itself and thus its volume calculable accurately. Variations in the size of cube may not affect the calculation because of the inventor's realization that tumors result in a deviation from behavior of functioning tissue. Since the volume of the functioning tissue is subtracted from the volume of cube, the remaining volume can correspond to a non-functioning tissue volume, which is likely to be a tumor volume. In some instances, confirmation of tumor can be done by IPS 60 based on the tracking techniques discussed above.

The volume of the circumscribing cube ($V_{CC}$) can be determined by the cube dimensions. It is understood that the circumscribing cube need not be touching the tumor and may be separated from the tumor by a variable margin. It is also understood that other shapes could be used such as a rectangular prism or an ellipsoid for the circumscribing volume.

The volume of functioning tissue ($V_{FT}$) can be derived from the concentration of isotope intensities. The concentration (C) can be calculated as the isotope intensities in functioning tissue ($I_{FT}$) divided by the volume of functioning tissue ($V_{FT}$), ie, $C=I_{FT}/V_{FT}$. Concentration can be determined by sampling functioning tissue. Concentration may be predetermined or calculated for a specific patient. Once concentration is known, the volume of functioning tissue is determined as $V_{FT}=I_{FT}/C$.

In some embodiments, tumor intensities are less (colder) than functioning tissue intensities. In another embodiment of the invention, tumor intensities are more (hotter) than functioning tissue intensities. It is understood that the circumscribing volume margins may be increased or decreased to optimize performance.

Warn Liver Cancer 213

The number, location, volumes and intensities of the suspected tumor masses are used to calculate a LC Warning index. Planned therapy may be used to remove suspected masses from the LC Warning index calculations.

Serial scans can be used to calculate changes in the number, location, volumes and intensities of the suspected tumor masses and to update the LC Warning index. A threshold on the LC Warning index can be used for signaling a LC Detection.

Terminology

Many other variations than those described herein will be apparent from this disclosure. For example, certain acts, events, or functions of any of the algorithms described herein can be performed in a different sequence, can be added, merged, or left out altogether (for example, not all described acts or events are necessary for the practice of the algorithms). Moreover, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

It is to be understood that not necessarily all such advantages can be achieved in accordance with any particular example of the examples disclosed herein. Thus, the examples disclosed herein can be embodied or carried out in a manner that achieves or optimizes one advantage or group of advantages as taught herein without necessarily achieving other advantages as may be taught or suggested herein.

The various illustrative logical blocks, modules, and algorithm steps described in connection with the examples disclosed herein can be implemented as electronic hardware, computer software, or combinations of both. The described functionality can be implemented in varying ways for each particular application, but such implementation decisions should not be interpreted as causing a departure from the scope of the disclosure.

The various illustrative logical blocks and modules described in connection with the examples disclosed herein can be implemented or performed by a machine including one or more hardware processors, such as a microprocessor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry or digital logic circuitry configured to process computer-executable instructions. In another example, a processor can include an FPGA or other programmable device that performs logic operations without processing computer-executable instructions. A hardware processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the examples disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, is generally intended to convey that certain examples include, while other examples do not include, certain features, elements and/or states. Thus, such conditional language is not generally intended to imply that features, elements and/or states are in any way required for one or more examples or that one or more examples necessarily include logic for deciding, with or without author input or prompting, whether these features, elements and/or states are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain examples require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various examples, it will be understood that various omissions, substitutions, and changes in the form and details of the devices or algorithms illustrated can be made without departing from the spirit of the disclosure. As will be recognized, the inventions described herein can be embodied within a form that does not provide all of the features and benefits set forth herein, as some features can be used or practiced separately from others.

Additionally, all publications, patents, and patent applications mentioned in this specification are herein incorporated by reference to the same extent as if each individual publication, patent, or patent application was specifically and individually indicated to be incorporated by reference.

What is claimed is:

1. A system for determining a tumor from image data obtained from a functional scanner, the system comprising one or more hardware processors configured to:
   determine a region of interest corresponding to an anatomical feature from image data taken at a first time;
   identify a portion within the region of interest that varies in intensity with its corresponding neighboring portion by a threshold;
   fit a shape from the identified portion that includes an entire volume of a suspected tumor mass;
   determine a first volume of the fitted shape based on dimensions of the fitted shape;
   determine a second volume of functional tissue within the fitted shape based on a concentration of isotope intensities;
   determine a third volume of the suspected tumor mass based on a difference between the determined first volume and the determined second volume;
   track the fitted shape over time with image data obtained at a second time of the suspected tumor mass; and
   determine that the suspected tumor mass corresponds to a tumor based on the tracking and that the third volume corresponds to the tumor's volume.

2. The system of claim 1, wherein the one or more hardware processors are further configured to determine the third volume of the tumor without identifying a boundary of the tumor.

3. The system of claim 2, wherein the volume of the tumor is further determined based on subtracting a functioning tissue volume in a shape including the tumor from the shape's volume.

4. The system of claim 1, wherein the fitted shape comprises a 3D ellipsoid.

5. The system of claim 1, wherein the fitted shape comprises a 3D tubular shape.

6. The system of claim 1, wherein the one or more hardware processors are further configured to determine that the fitted shape corresponds to a blood vessel or a cyst.

7. The system of claim 1, wherein the one or more hardware processors are further configured to pre-process the image data.

8. The system of claim 7, wherein the pre-processing comprises at least one or more of: boosting resolution, sharpening, slicing, or dicing.

9. The system of claim 1, wherein the one or more hardware processors are further configured to display results of the determination.

10. A method for determining a tumor from image data obtained from a functional scanner, the method comprising:
    determining a region of interest corresponding to an anatomical feature from image data taken at a first time;
    identifying a portion within the region of interest that varies in intensity with its corresponding neighboring portion by a threshold;
    fitting a shape from the identified portion that includes an entire volume of a suspected tumor mass;
    determining a first volume of the fitted shape based on dimensions of the fitted shape;
    determining a second volume of functional tissue within the fitted shape based on a concentration of isotope intensities;
    determining a third volume of the suspected tumor mass based on a difference between the determined first volume and the determined second volume;
    tracking the fitted shape over time with image data obtained at a second time of the suspected tumor mass; and
    determining that the suspected tumor mass corresponds to a tumor based on the tracking and that the third volume corresponds to the tumor's volume.

11. The method of claim 10, further comprising determining a volume of the tumor without identifying a boundary of the tumor.

12. The method of claim 11, wherein the volume of the tumor is further determined based on subtracting a functioning tissue volume in a shape including the tumor from the shape's volume.

13. The method of claim 10, further comprising determining that the fitted shape corresponds to a blood vessel or a cyst.

14. The method of claim 10, further comprising pre-processing the image data.

15. The method of claim 10, wherein the region of interest correspond to a liver.

16. A system of determining a tumor volume from image data obtained from a functional scanner, the system comprising one or more hardware processors configured to:
    identify a portion within a region of interest corresponding to a liver that varies in intensity with its corresponding neighboring portion by a threshold; and
    determine a volume of the portion without identifying a boundary of the portion wherein the determination of said volume of the portion comprises:
        determining a first volume of a shape that includes the identified portion; and
        determining a second volume of a functional tissue within the shape based on a concentration of isotope intensities;

wherein is the volume of the portion is based on a difference between the determined first volume and the determined second volume.

17. The system of claim 16, wherein the volume is confirmed as a tumor based on fitting a shape from the identified portion.

18. The system of claim 17, wherein the volume is further confirmed as the tumor based on tracking the portion over time.

* * * * *